(12) United States Patent
Kneissl

(10) Patent No.: US 11,660,080 B2
(45) Date of Patent: May 30, 2023

(54) BIOPSY GUN

(71) Applicant: PETER PFLUGBEIL GMBH, Zorneding (DE)

(72) Inventor: Florian Kneissl, Munich (DE)

(73) Assignee: PETER PFLUGBEIL GMBH, Zorneding (DE)

( * ) Notice: Subject to any disclaimer, the term of this patent is extended or adjusted under 35 U.S.C. 154(b) by 639 days.

(21) Appl. No.: 16/334,154

(22) PCT Filed: Sep. 15, 2017

(86) PCT No.: PCT/EP2017/073242
§ 371 (c)(1),
(2) Date: Jun. 5, 2019

(87) PCT Pub. No.: WO2018/050805
PCT Pub. Date: Mar. 22, 2018

(65) Prior Publication Data
US 2019/0307435 A1    Oct. 10, 2019

(30) Foreign Application Priority Data
Sep. 16, 2016 (DE) ..................... 20 2016 105 165.7

(51) Int. Cl.
*A61B 10/02* (2006.01)
*A61B 90/00* (2016.01)

(52) U.S. Cl.
CPC ...... *A61B 10/0275* (2013.01); *A61B 10/0266* (2013.01); *A61B 90/06* (2016.02); *A61B 2010/0208* (2013.01)

(58) Field of Classification Search
CPC ..... A61B 5/02; A61B 5/0233; A61B 10/0266; A61B 10/0275; A61B 2010/0208; A61B 90/06
See application file for complete search history.

(56) References Cited

U.S. PATENT DOCUMENTS 5,842,999 A    12/1998   Pruitt et al.
2004/0097830 A1  5/2004  Cooke et al.
(Continued)

FOREIGN PATENT DOCUMENTS

DE    10 2008 038414 A1    2/2010
DE    20 2011 004277 U1    7/2011

OTHER PUBLICATIONS

International Search Report and Written Opinion dated Mar. 15, 2018 corresponding to International Patent Application No. PCT/EP2017/073242, and English translation thereof.

*Primary Examiner* — Patrick Fernandes
*Assistant Examiner* — Severo Antonio P Lopez
(74) *Attorney, Agent, or Firm* — Squire Patton Boggs (US) LLP

(57) ABSTRACT

A biopsy gun having a cannula and a stylet guided in the cannula comprises the following a housing, a cannula carriage for moving the cannula, a stylet carriage for moving the stylet, a tensioning grip for tensioning the cannula carriage and the stylet carriage from an initial position into a tensioning position, and an engaging member that is provided on the tensioning grip and has recesses adapted to engage with corresponding projections of the cannula carriage and the stylet carriage. The engaging member is rotatably attached to the tensioning grip and is biased by a spring against a contact surface of the housing.

2 Claims, 16 Drawing Sheets

(56) References Cited

U.S. PATENT DOCUMENTS

| | | |
|---|---|---|
| 2004/0097832 A1 | 5/2004 | Adams et al. |
| 2004/0158172 A1* | 8/2004 | Hancock ............ A61B 10/0275 600/564 |
| 2012/0078133 A1 | 3/2012 | Nicoson et al. |
| 2015/0105690 A1 | 4/2015 | Hathaway |
| 2015/0148704 A1* | 5/2015 | Swick ................ A61B 10/0275 600/567 |

* cited by examiner

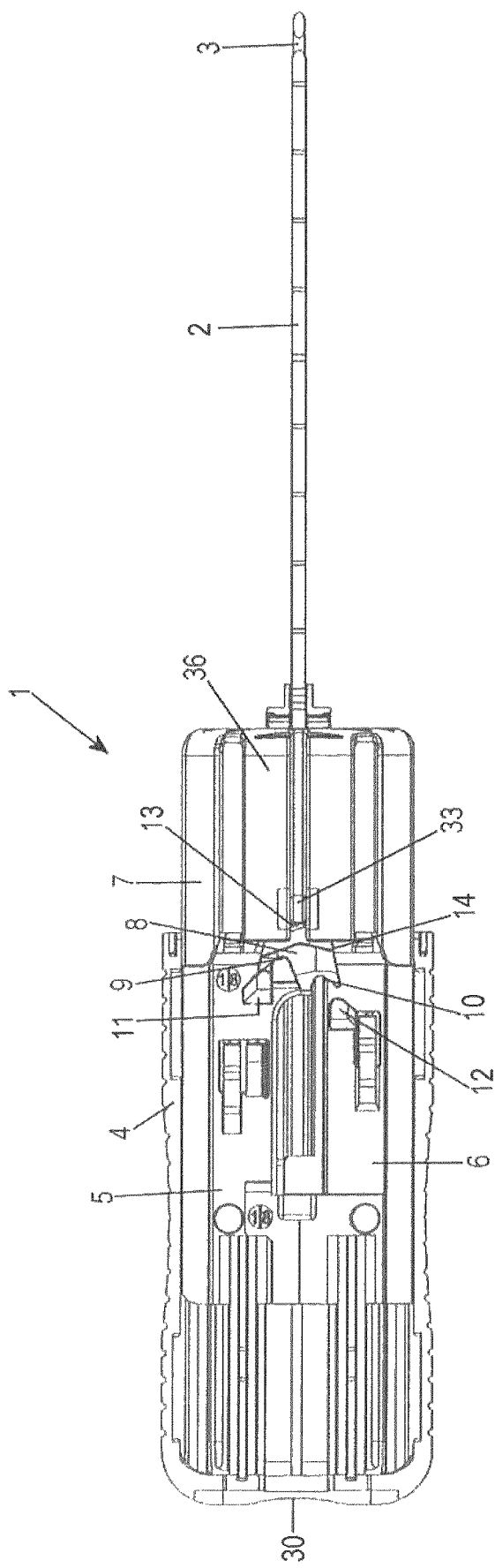

BIOPSY GUN

The prior art already describes a manually tensionable biopsy gun, in which a cannula and a stylet guided in the cannula can be tensioned by means of two successive strokes of a tensioning grip. For this purpose, the cannula is fixed to a cannula carriage and the stylet is fixed to a stylet carriage, and both carriages are arranged next to each other in a housing of the biopsy gun and are slidably supported in the housing in the longitudinal direction of the housing of the biopsy gun. The tensioning grip has an elongate element that is attached to the tensioning grip in a torque-proof manner and can be bent laterally. At the front end of the elongate element, two teeth adapted to engage in the corresponding recesses of the cannula carriage or the stylet carriage are laterally formed.

When the cannula carriage and the stylet carriage are in a relaxed state, the respective tooth of the elongate element is engaged with the recess of the cannula carriage, so that, during the tensioning of the cannula carriage, the elongate element is bent in the transverse direction to allow the tooth corresponding to the recess of the stylet carriage to be guided past the recess of the stylet carriage and, in the first stroke, only the cannula carriage is biased, but not the stylet carriage.

After the cannula carriage has been biased and the tensioning grip returns to its relaxed initial position, also the bent state of the elongate element is reset so that, in the second stroke, the other tooth corresponding to the recess of the stylet carriage engages therewith and, thus, the stylet carriage can be biased.

The elongate element has to have a minimum length for allowing it to be bent sufficiently easily in the transverse direction. This leads to the entire biopsy gun having a minimum length that may make it harder to bias the biopsy gun in a convenient way by using one hand only.

It is therefore a first object of the present invention to provide an improved biopsy gun having a shorter length.

In addition, such biopsy guns usually have two keys, namely, a first key solely for triggering the stylet and a second key for subsequently triggering the cannula if the stylet has already been triggered, or for the time-staggered triggering of stylet and cannula. So as to allow the second key to not only trigger the cannula but also the stylet, either a further component is required, or a snap-in hook of the stylet carriage has to be designed such that it is not only operable by the first key but also by the second key. Both variants render the design of the biopsy gun complicated.

It is therefore a second object of the present invention to provide an improved biopsy gun having a less complex design.

It is a third object of the present invention to create a biopsy gun that can be easily assembled while being robust at the same time.

A fourth object of the present invention consists in creating a biopsy gun that can be securely biased and triggered even if components having a comparatively low rigidity are used.

A fifth object of the invention consists in creating a biopsy gun that can be biased securely.

According to the invention, these objects are achieved by claims 1, 5, 8, 9 and 12, respectively.

In the following, an embodiment of the invention is described with reference to the following Figures, in which.

Figure 4A:
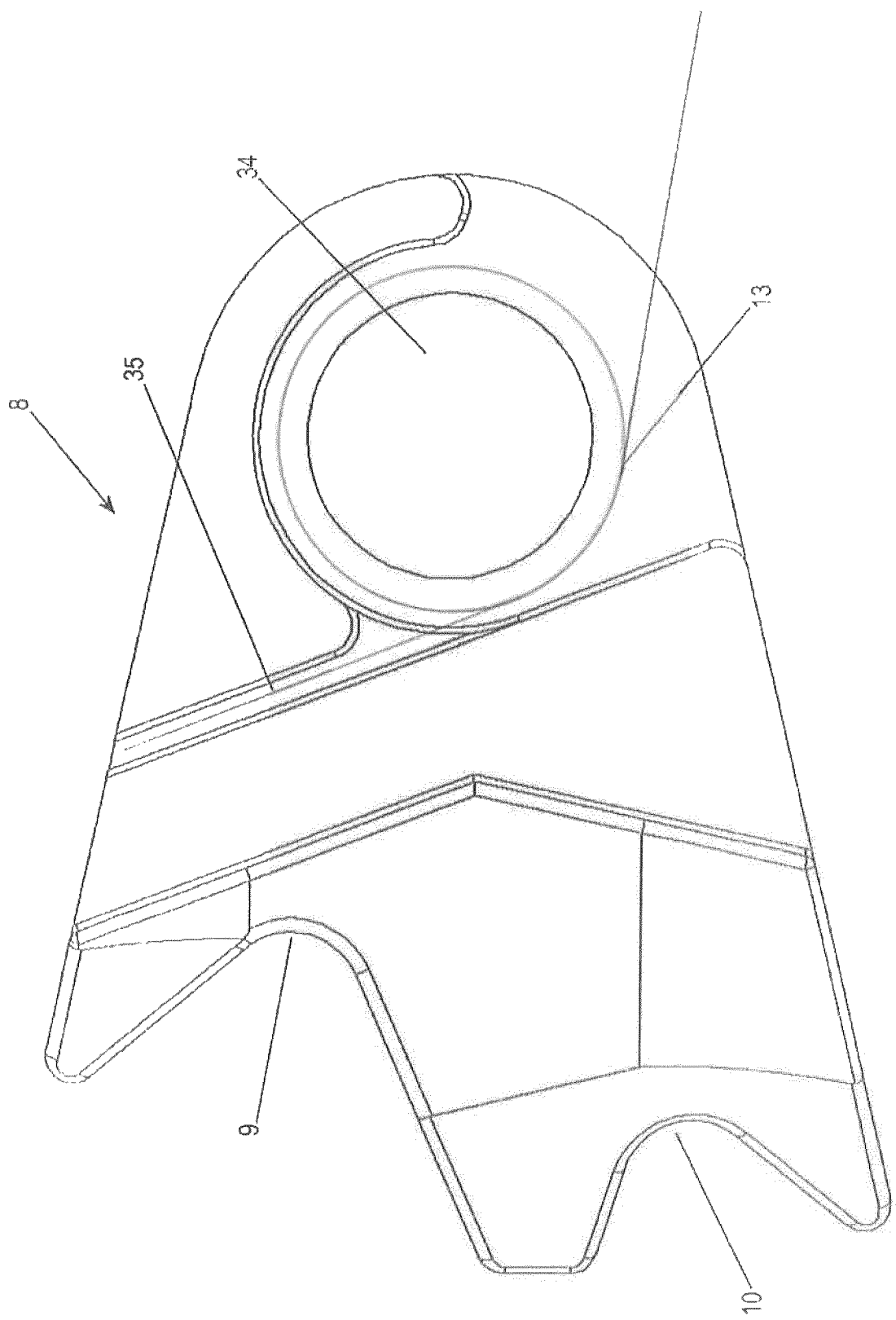
Figure 4B:
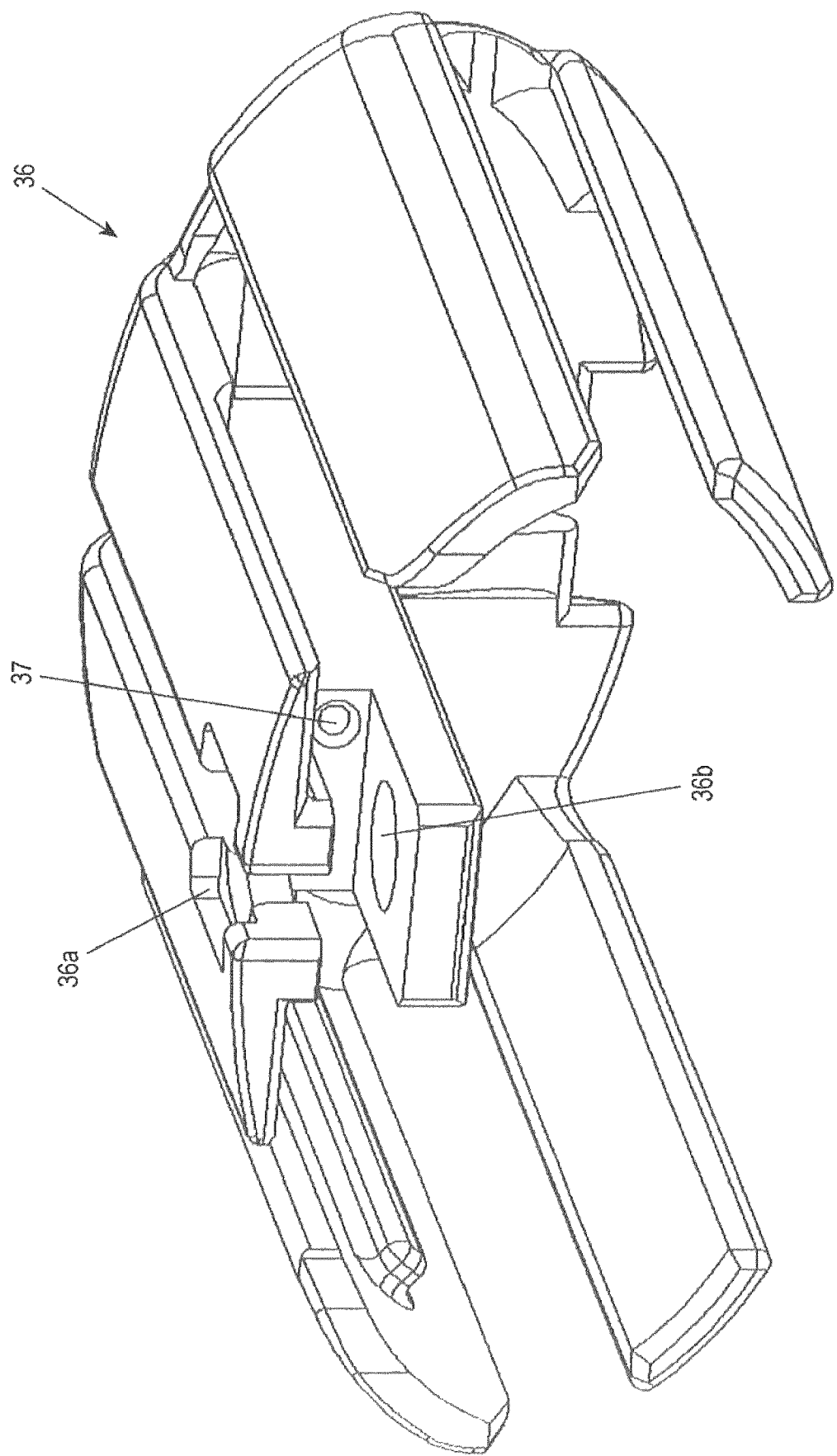
Figure 4C:
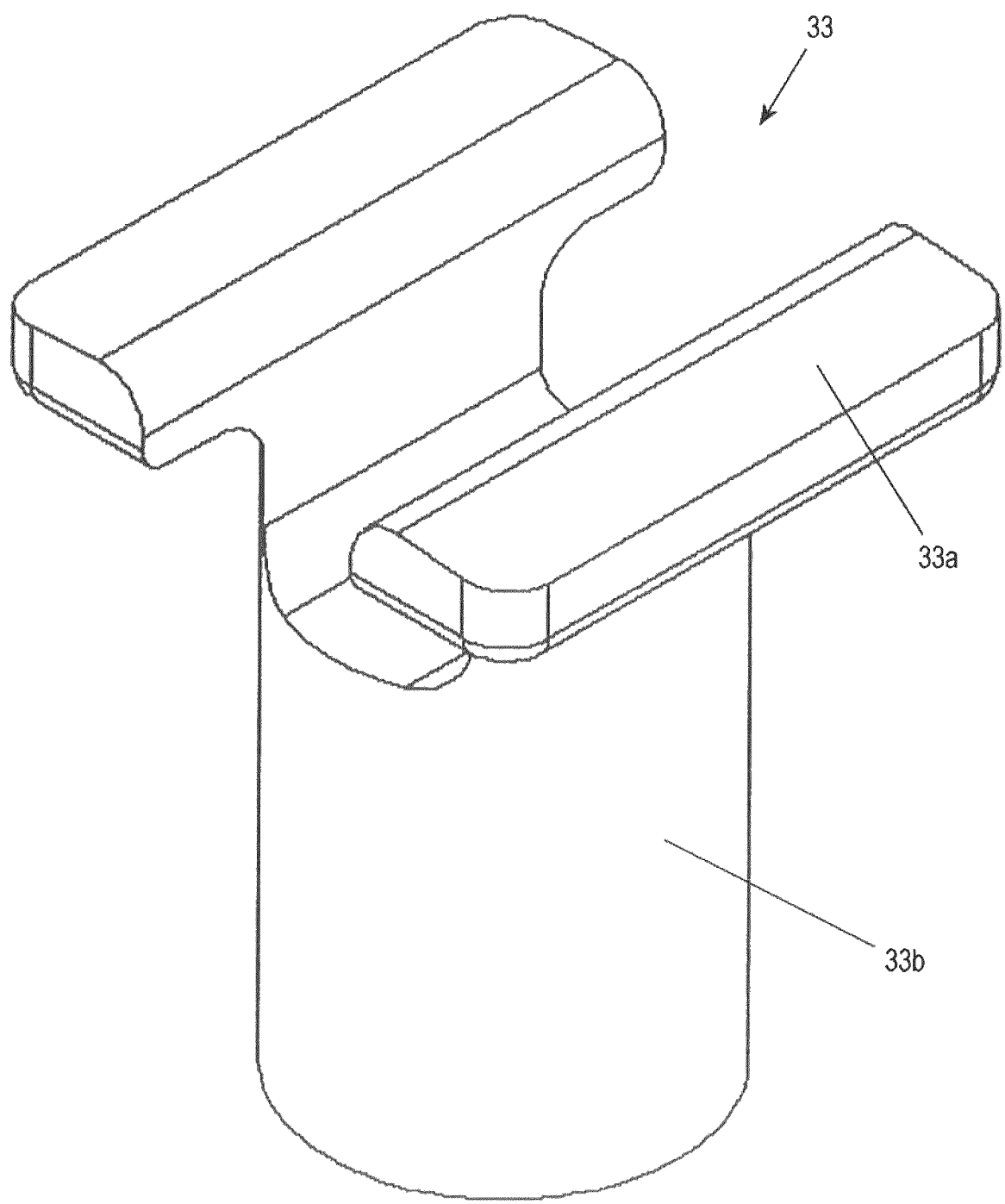
Figure 5:
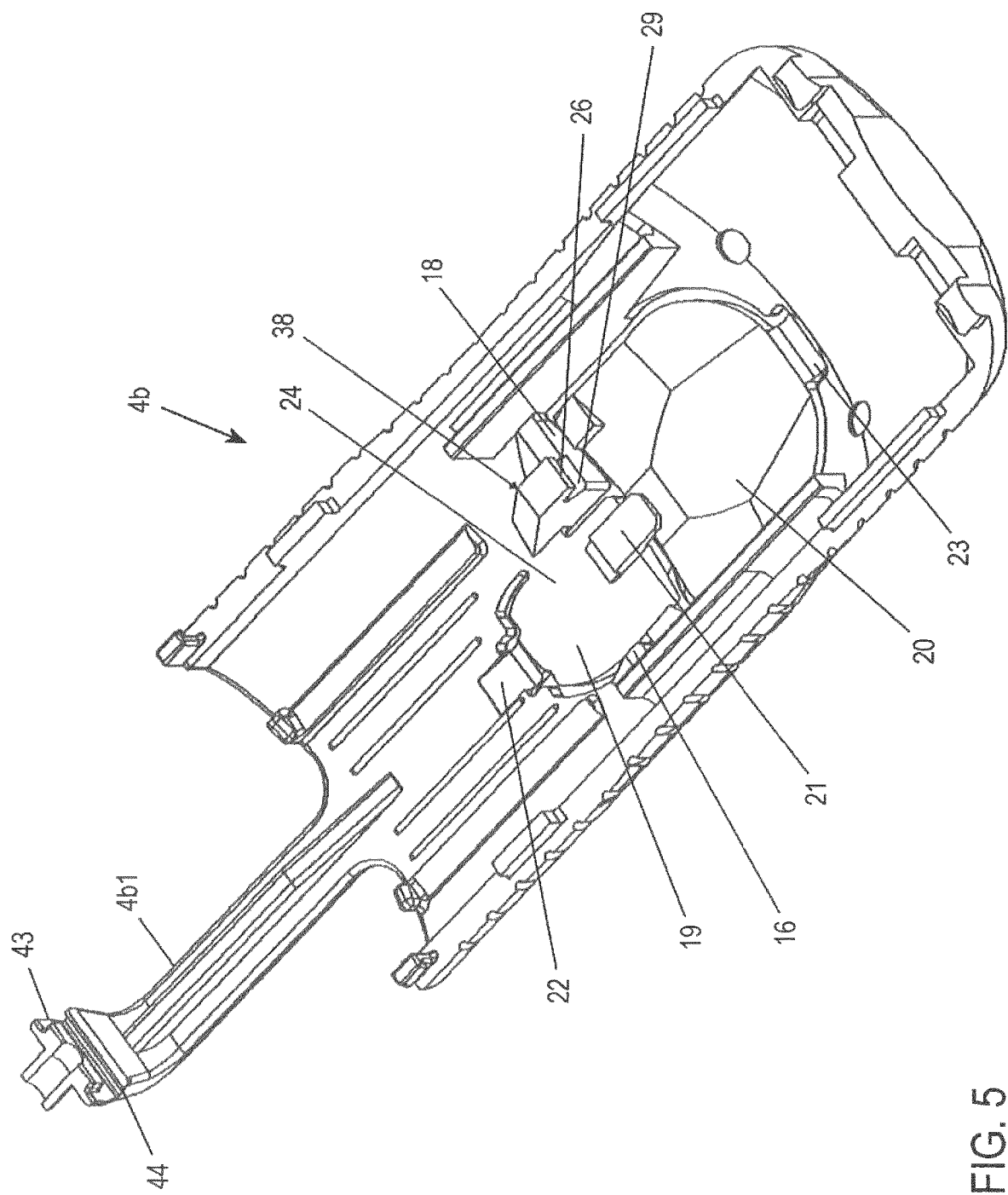
Figure 6:
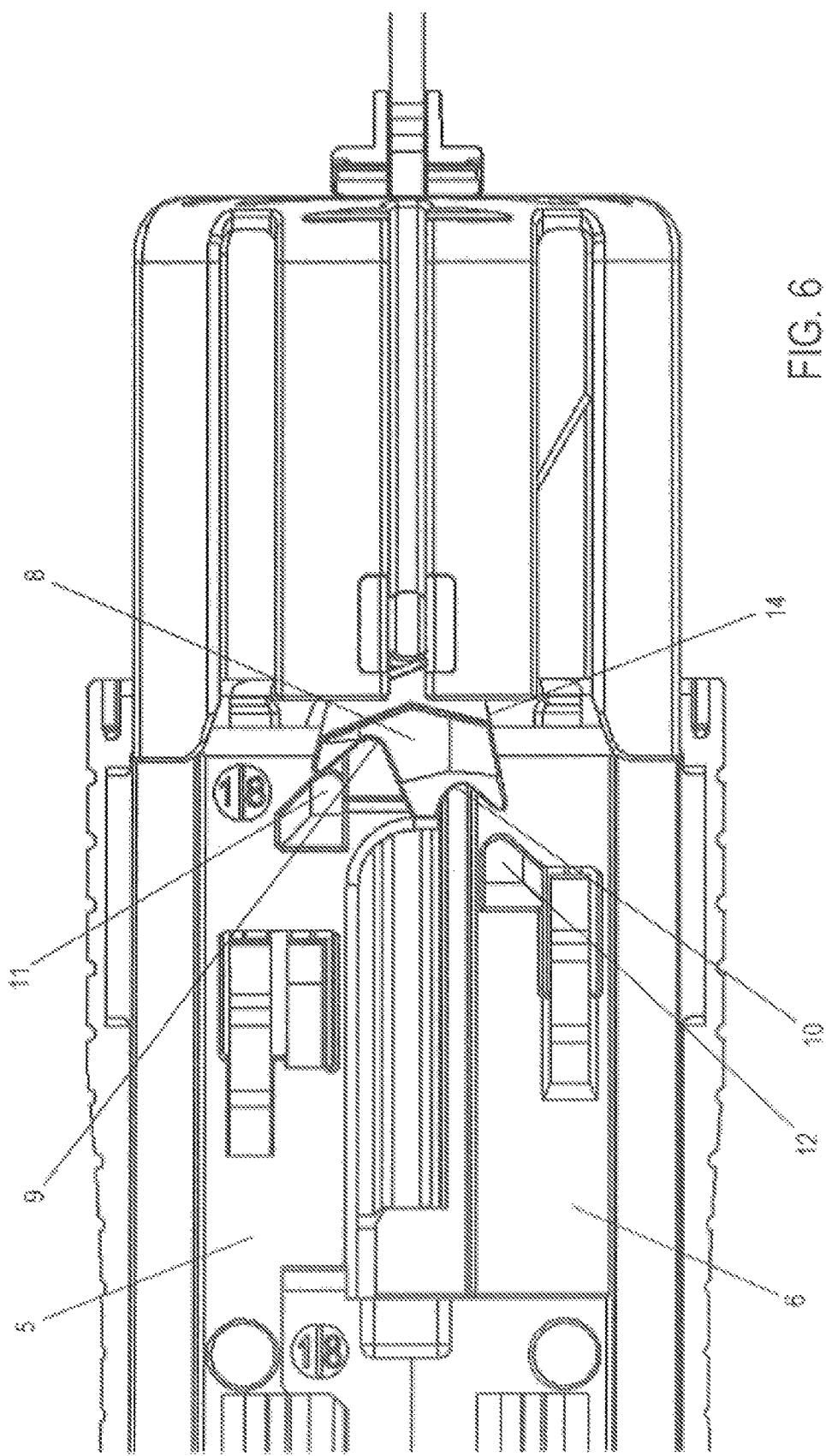
Figure 7:
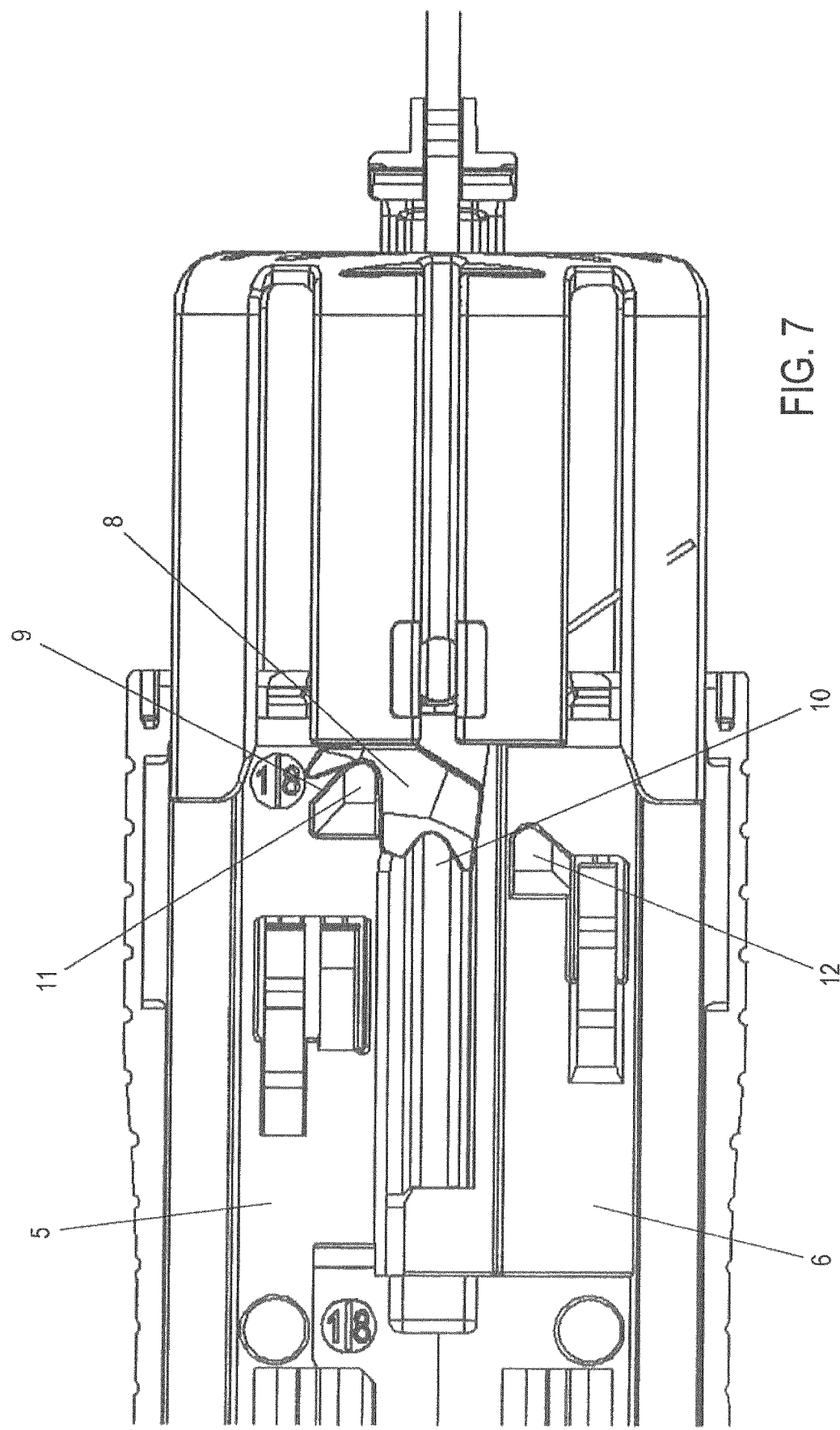
Figure 8:
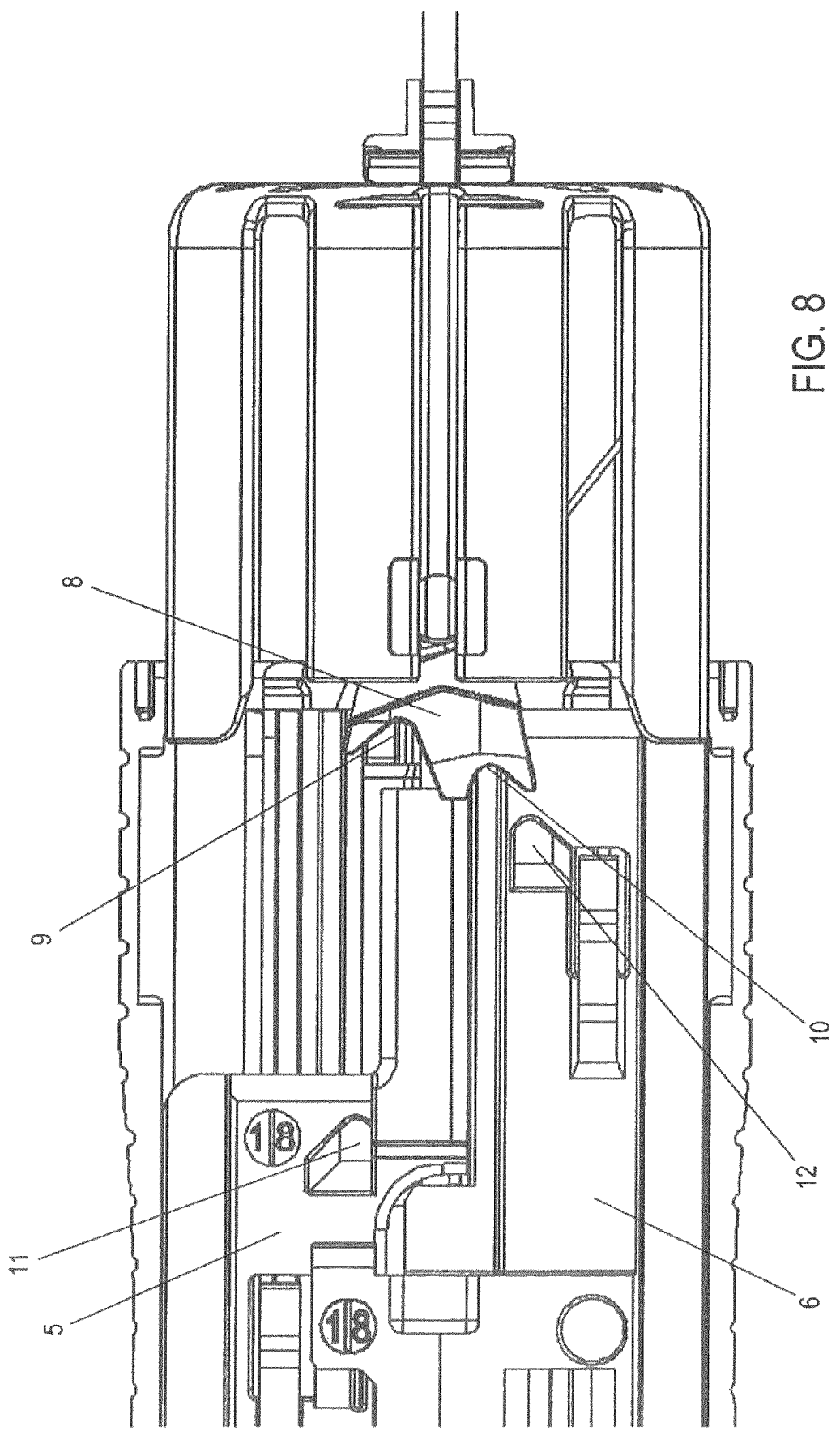
Figure 9:
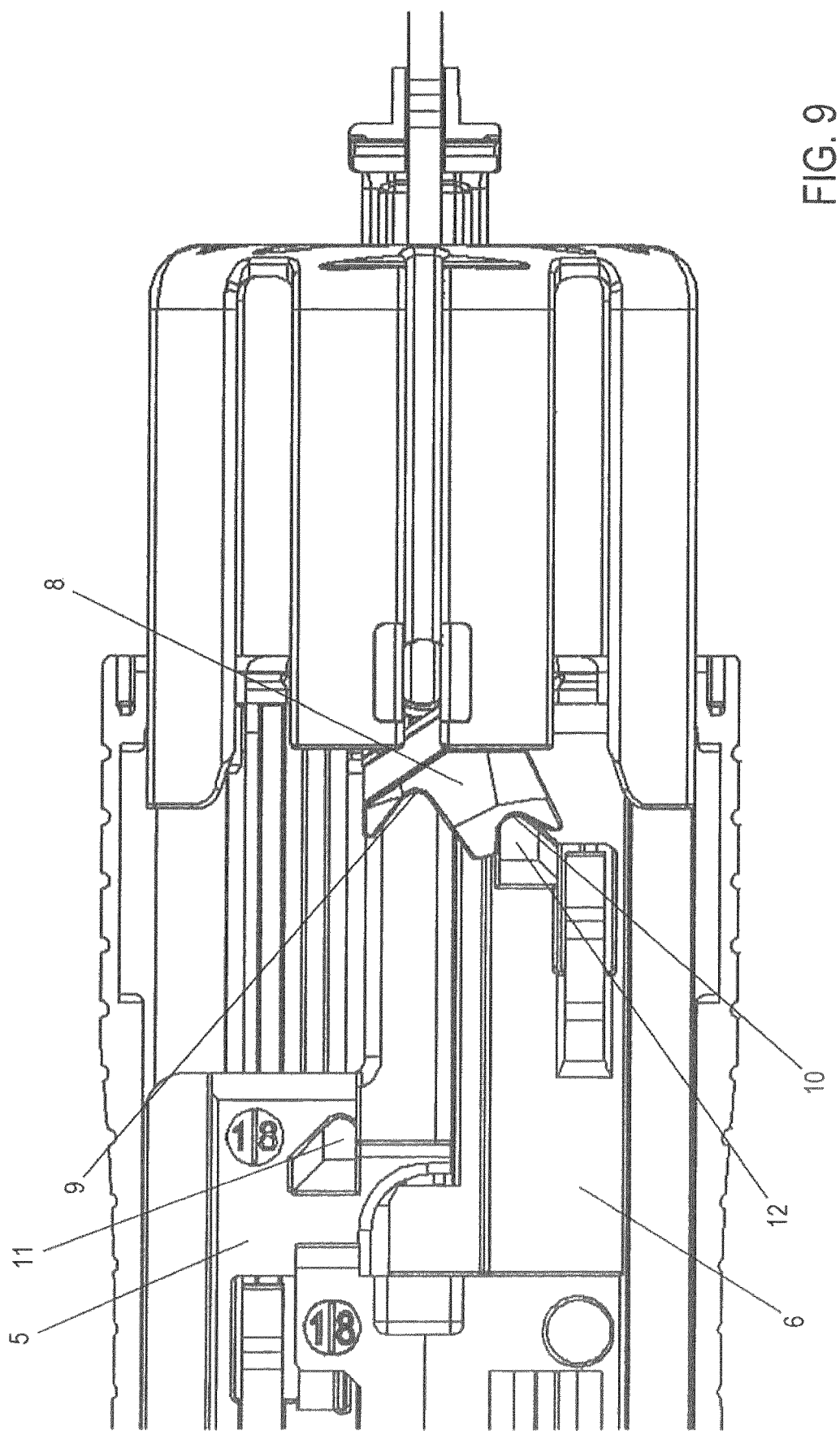
Figure 10:
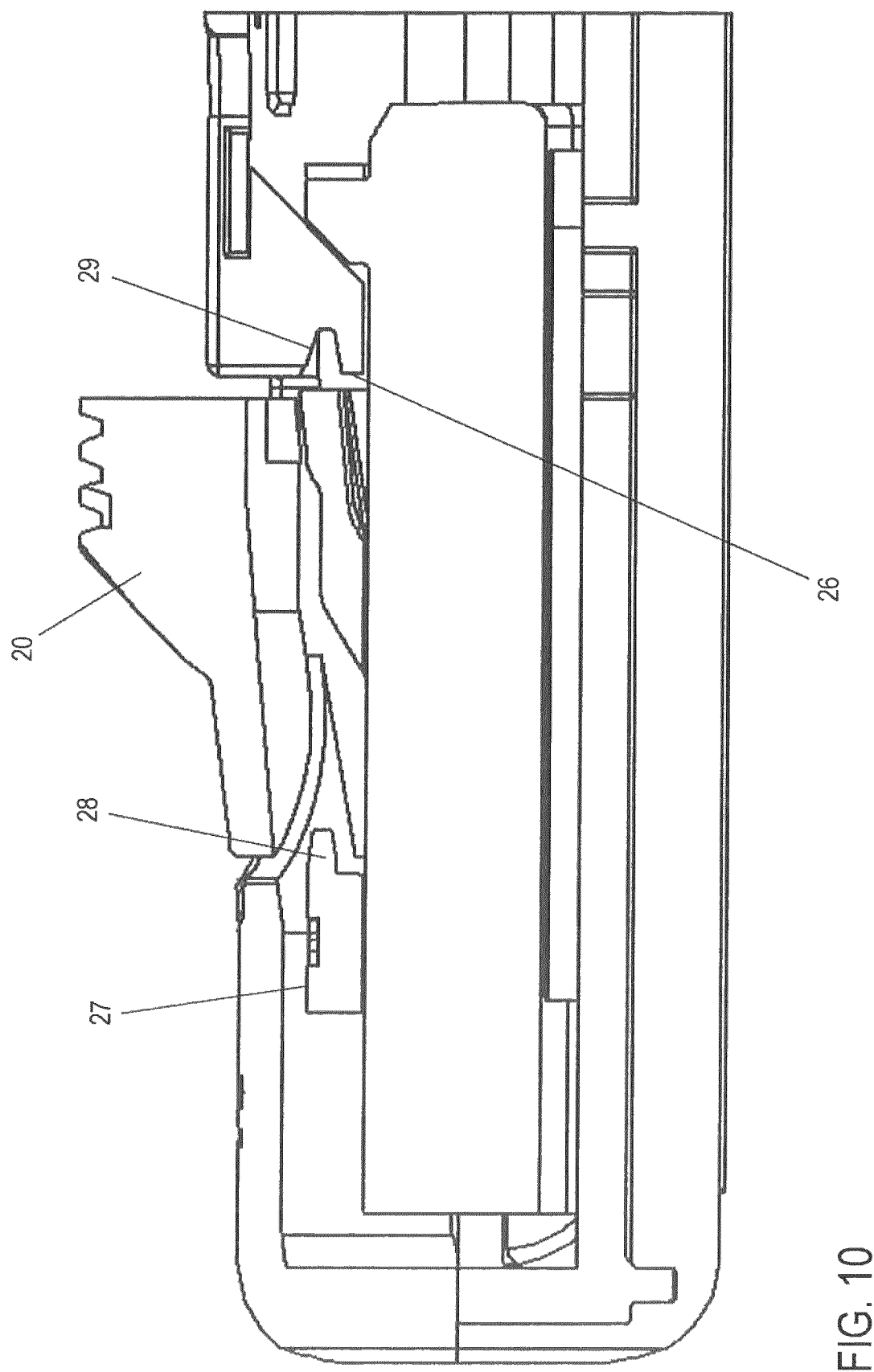
Figure 11:
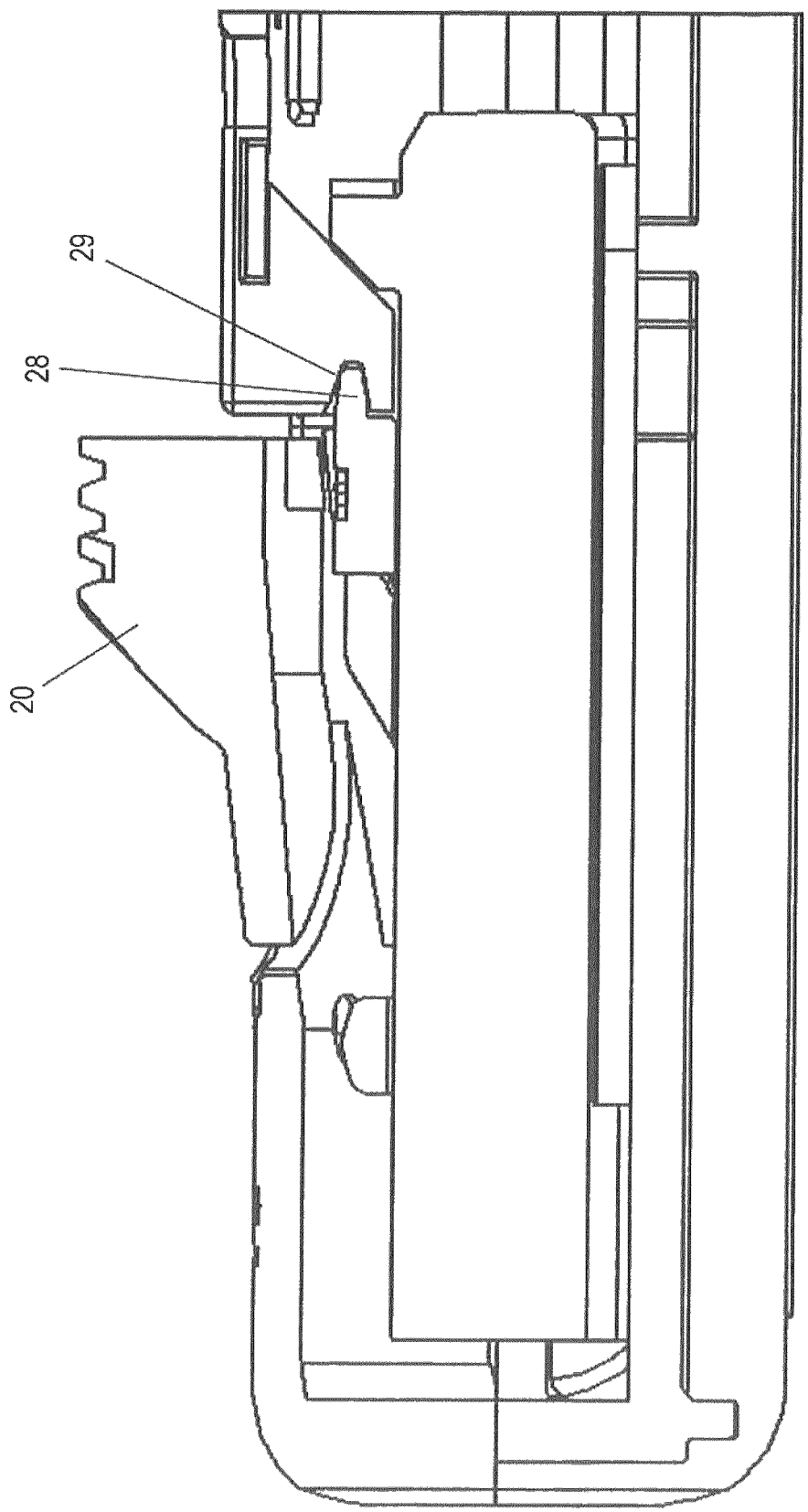
Figure 12:
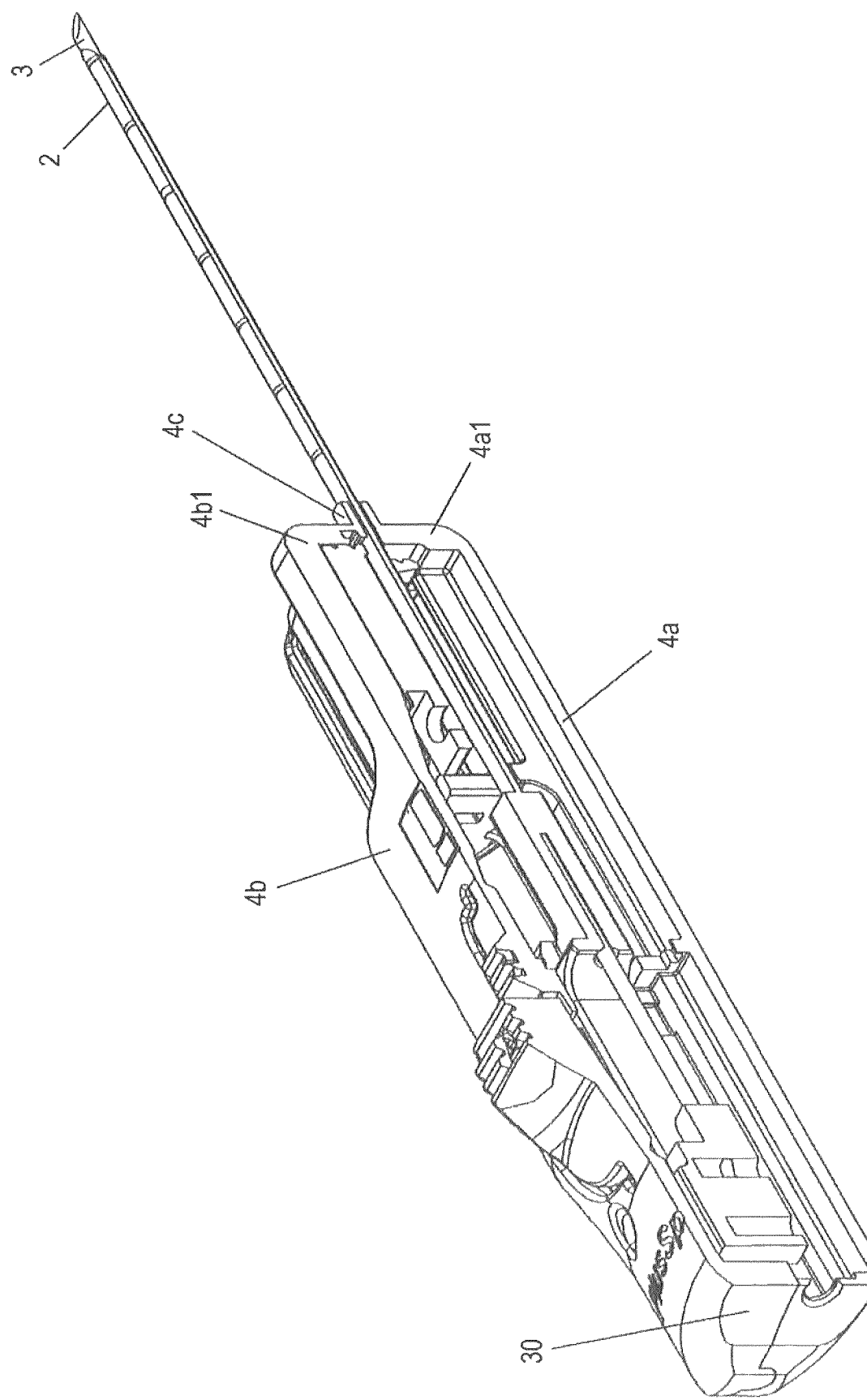

FIG. 4 is a top view of the biopsy gun without the upper half-shell of the housing but with the tensioning grip; FIG. 4a is a top view of an engaging member; FIG. 4b is a perspective view of the tensioning grip; FIG. 4c is a perspective view of a pin;

FIG. 5 is a perspective inner view of the upper half-shell of the housing;

FIG. 6 is a top view of a section of the biopsy gun without the upper half-shell of the housing in the state in which the tensioning grip is in its initial position;

FIG. 7 is a top view of a section of the biopsy gun without the upper half-shell of the housing in the state in which the tensioning grip has been slightly advanced in a first stroke, so that a cannula carriage is tensioned;

FIG. 8 is a top view of a section of the biopsy gun without the upper half-shell of the housing in the state in which the cannula carriage has been tensioned and the tensioning grip has returned to its initial position;

FIG. 9 is a top view of a section of the biopsy gun without the upper half-shell of the housing in the state in which the tensioning grip has been slightly advanced in a second stroke, so that a stylet carriage is tensioned;

FIG. 10 is a horizontal longitudinal section through the biopsy gun in a state in which the stylet carriage is tensioned;

FIG. 11 is a horizontal longitudinal section through the biopsy gun in a state in which the stylet carriage has been triggered/is not tensioned;

FIG. 12 shows a vertical longitudinal section through the biopsy gun.

In the following description, the longitudinal direction of the biopsy gun refers to the direction of cannula and stylet, the side with cannula and stylet being the front side. The transverse direction extends in the direction in which the cannula carriage and the stylet carriage are arranged next to each other, and the vertical direction extends perpendicularly to these two directions, the side with the keys being referred to as the upper side.

Figure 1:
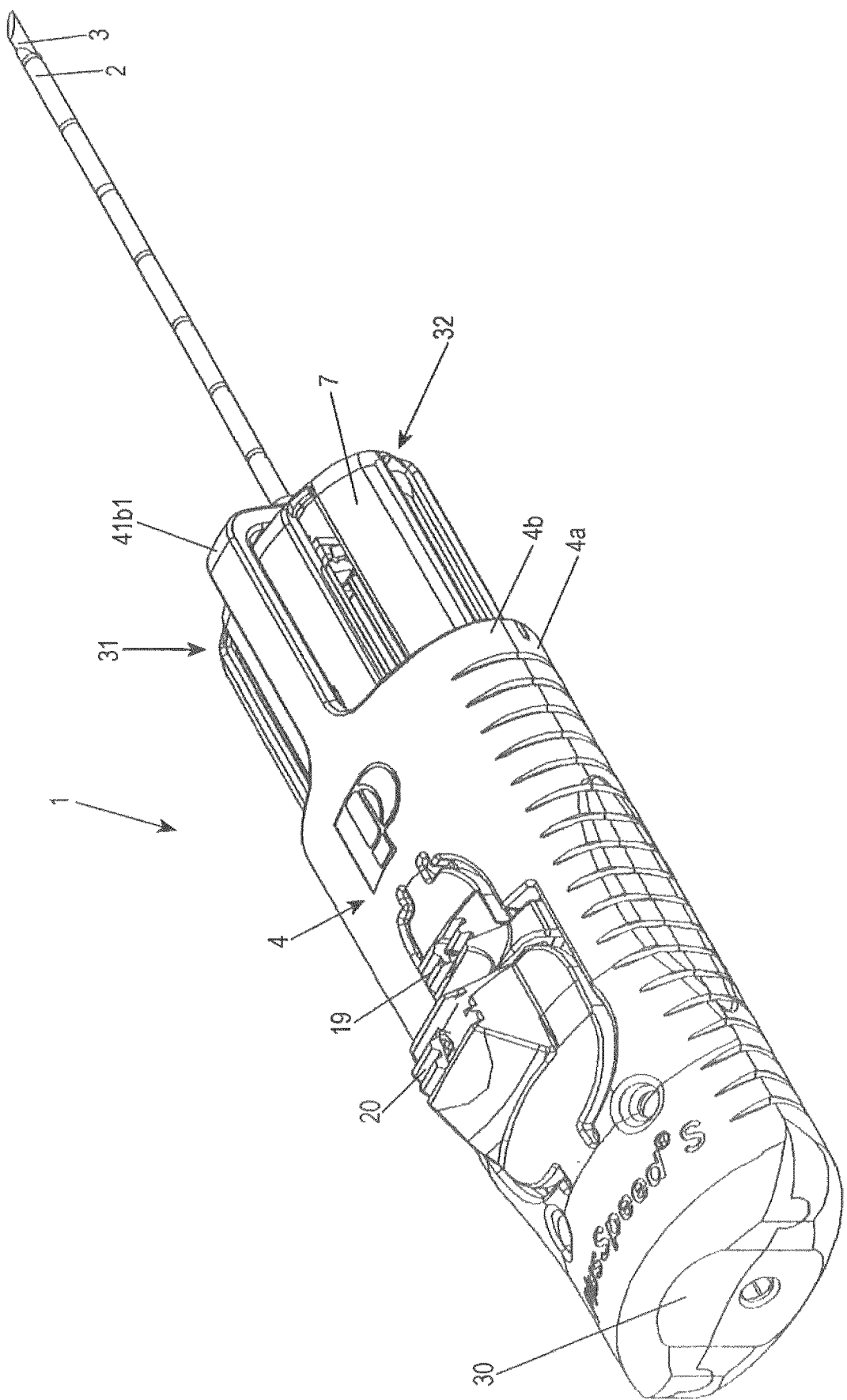
FIG. 1 is a perspective view of a biopsy gun according to the embodiment.

FIG. 1 shows a biopsy gun 1 having a housing 4, a tensioning grip 7, a cannula 2 and a stylet 3. The cannula 2 and the stylet 3 can be biased separately by operating the tensioning grip 7 twice. The tensioning grip 7 is accessible to the index finger and the middle finger of an operator's hand through two openings 31, 32 of the housing 4, whereas the operator's thumb is placed in a non-slip manner in the recess 30 provided therefor at the other end of the housing 4. The housing 4 basically consists of two half-shells 4a, 4b, and L-shaped frame elements 4a1, 4b1 of the two half-shells 4a, 4b are disposed between the openings 31, 32 of the housing, respectively. Furthermore, FIG. 1 shows a first key 19 for triggering the stylet and a second key 20 for triggering the cannula.

Figure 2A:
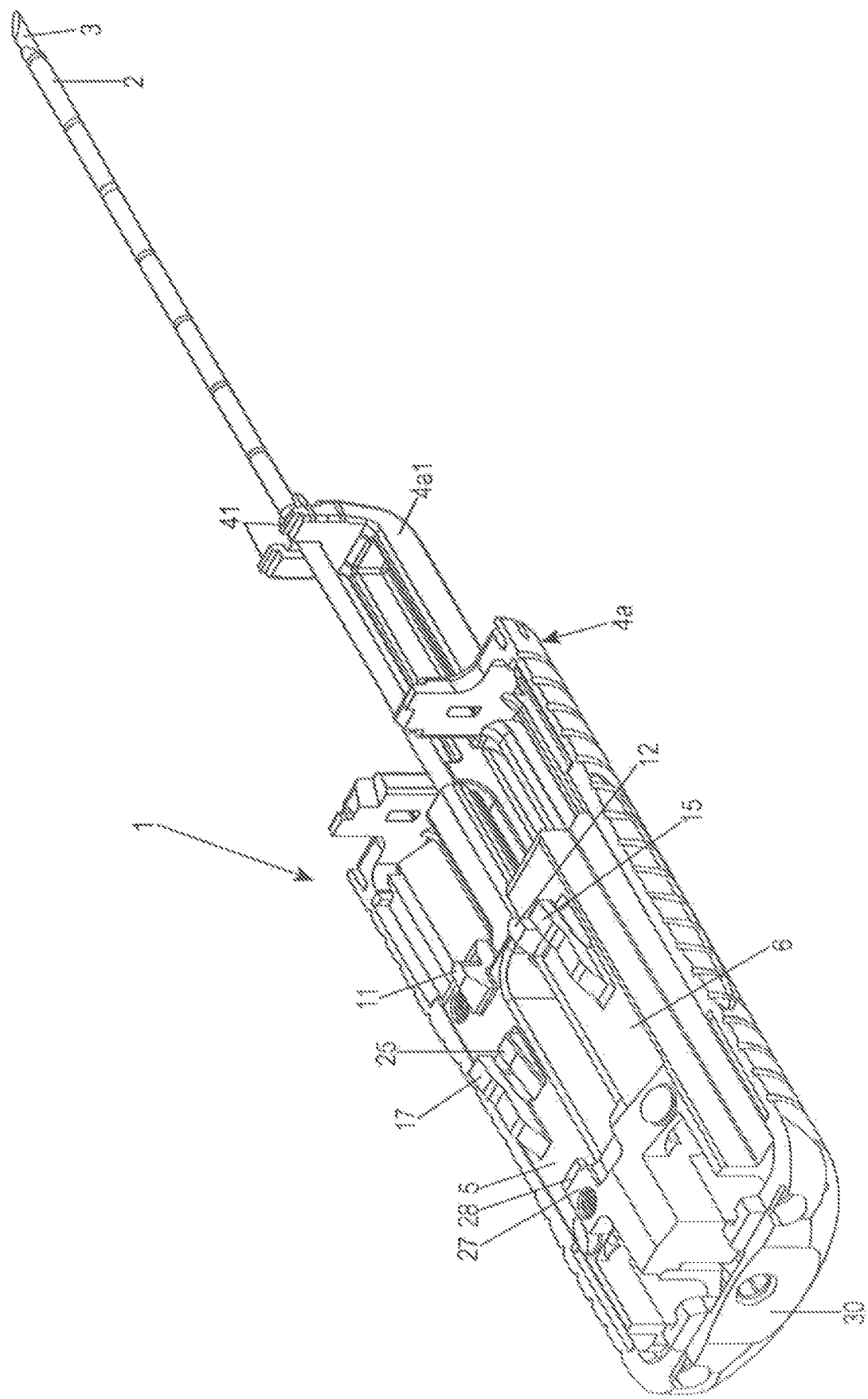
FIG. 2a is a perspective view of the biopsy gun without the upper half-shell of the housing and without the tensioning grip.
Figure 2B:
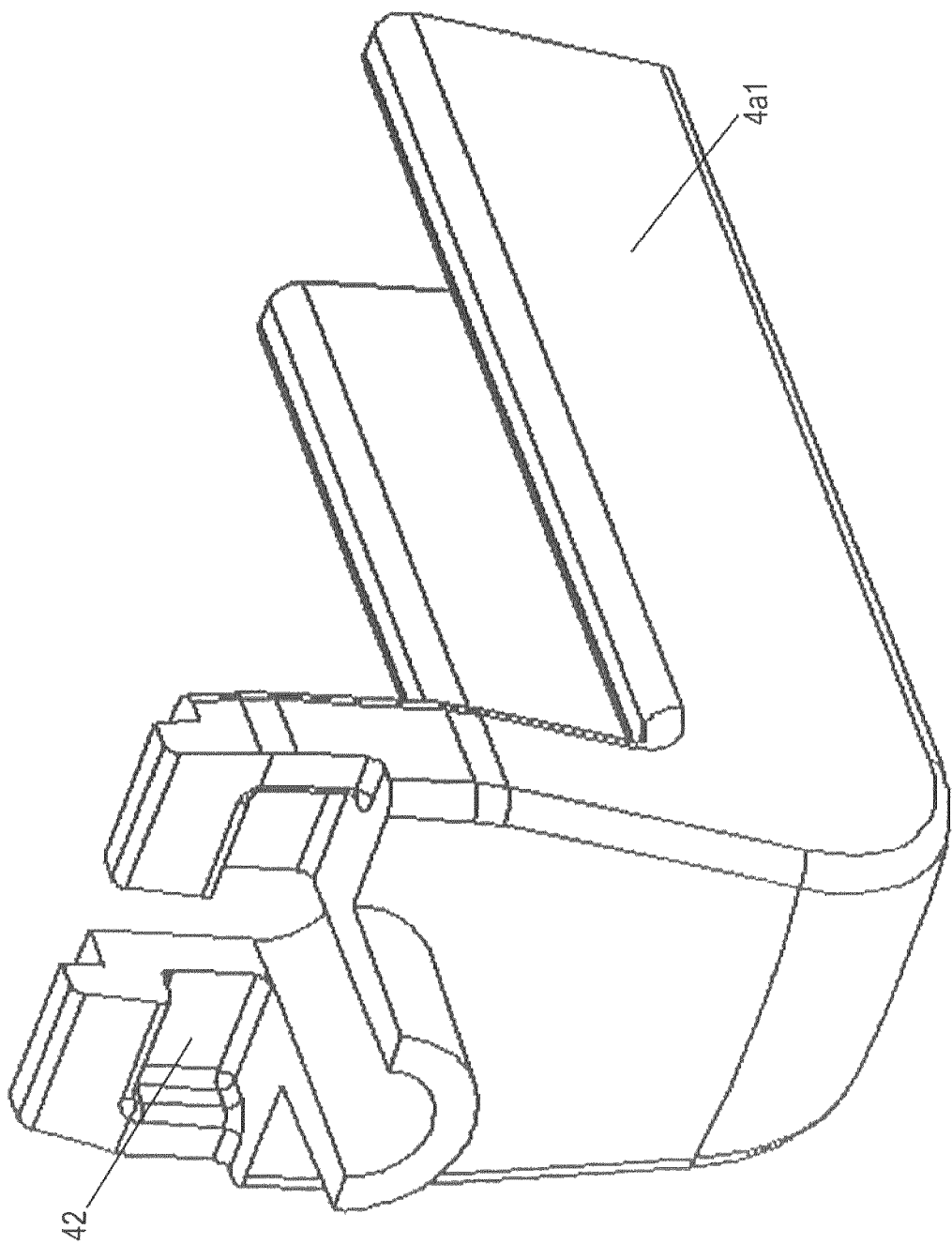
FIG. 2b is a perspective view of a frame element of the lower shell of the housing.

FIG. 2 shows the biopsy gun 1 without the tensioning grip 7 and without the upper half-shell 4b of the housing. Furthermore, the biopsy gun 1 has a cannula carriage 5 that is connected to the cannula 2, and a stylet carriage 6 that is connected to the stylet 3. Both carriages can be injection-molded components being directly injection-molded onto the cannula or the stylet. The carriages are guided on respective rails (not shown) and are biased forwards by respective coil springs (not shown).

The cannula carriage 5 has a cannula-side projection 11 extending upwards from the upper surface of the cannula carriage 5. In this embodiment, the cannula-side projection 11 is rounded off at its front side, and it has stabilizing inclined surfaces rearwards and outwards.

Further rearwards, the cannula carriage 5 has a first cannula snap-in hook 17 on its side which is outside in the transverse direction and a second cannula snap-in hook 25 on its side that is inside in the transverse direction. Both cannula snap-in hooks 17, 25 are fastened resiliently in the vertical direction, so that they can be pressed down in the vertical direction. This resilient connection is effected by the cannula snap-in hooks 17, 25 projecting and being formed integrally with the cannula carriage 5.

The stylet carriage 6 has a stylet-side projection 12 projecting upwards from the upper surface of the cannula carriage 6. In this embodiment, the stylet-side projection 12 is rounded off at its front side and has stabilizing inclined surfaces rearwards and outwards.

Further rearwards, the stylet carriage 6 has a stylet snap-in hook 15, which is resiliently fastened in the vertical direction, so that it can be pressed down in the vertical direction. This resilient connection is effected by the stylet snap-in hook 15 projecting and being formed integrally with the stylet carriage 6.

Besides, the stylet carriage 6 has a trigger element 27 having a lug 28 projecting forwards, said lug being disposed on a common longitudinal axis with the second cannula snap-in hook 25 with respect to the transverse direction.

FIG. 4 shows the biopsy gun having a tensioning grip 7 on which an engaging member 8 is rotatably mounted. As can be seen in FIG. 4*a*, the engaging member 8 has a substantially triangular form in the top view, the front tip of which has a through-hole 34 and the rear tips of which have a cannula-side recess 9 and a stylet-side recess 10. Furthermore, the engaging member 8 is stronger in the area of the recesses 9 and 10 than in the area of the through-hole 34. In addition, in the less strong area around the engaging hole 34, there is a spring-receiving groove 35 in which a first end of a coil spring 13 can be accommodated while the coil spring 13 surrounds the through-hole 34.

FIG. 4*b* shows a section 36 of the tensioning grip 7, which rotatably supports the engaging member 8. For this purpose, the section 36 has a rectangular seat 36*a* in an upper part of the section 36 and a through-hole 36*b* in a lower part of the section 36. Moreover, a spring-receiving hole 37 extending in the longitudinal direction is formed in the section 36; said hole is provided in the vertical direction between the upper part and the lower part of the section 36, and a second spring end can be introduced into it.

FIG. 4*c* shows a pin 33 having a cylindrically lower portion 33*b* and an upper portion 33*a* with a substantially rectangular contour.

The engaging member 8 is mounted on the tensioning grip 7 such that the spring 13 surrounds the through-hole 34 and the first spring end is accommodated in the spring-receiving groove 35. Furthermore, the second spring end is introduced into the spring-receiving hole 37, and the cylindrical portion 33*b* of the pin 33 penetrates the through-hole 34 of the engaging member 8 as well as the through-hole 36*b* of the section 36 while the upper portion 33*b* having a rectangular contour is received in the rectangular seat 36*a*. In this way, the engaging member 8 is rotatably supported on the section 36 of the tensioning grip 7, the engaging member 8 being initially biased by the coil spring 13 in the direction of the stylet carriage 6.

Furthermore, the tensioning grip 7 having the engaging member 8 mounted thereon is mounted on the housing 4 such that the engaging member 8 gets into contact with a contact surface 14 when the tensioning grip is tensioned into the initial position by a coil spring (not shown). By the contact of the engaging member 8 with the contact surface 14, the engaging member 8 is rotated in the initial position of the tensioning grip 7 against the force of the spring 13 away from the stylet carriage and towards the cannula carriage. This position is shown in an enlarged version in FIG. 6.

FIG. 6 shows that, in the initial position of the tensioning grip 7, the outer peripheral area of the recess 9 of the engaging member 8 is in contact with the cannula-side projection 11 such that the engaging member 8 is rotated by an operation of the tensioning grip 7 out of its initial position against the force of the spring 13 further towards the cannula carriage 5. In this way, the recess 9 gets into safe engagement with the cannula-side projection 11 (see FIG. 7), so that the cannula carriage 5 is moved along by the movement of the tensioning grip 7.

As is further shown in FIG. 7, the rotation of the engaging member 8 towards the cannula carriage allows the engaging member 8 to be safely guided past the stylet-side projection 12 without engaging therewith. In this way, it is ensured that only the cannula carriage 5 is tensioned in this first stroke.

After the cannula carriage 5 has been tensioned and locked with the housing 4 (will be described in more detail below), the tensioning grip 7 returns to its initial position, which is shown in FIG. 8. As the cannula carriage 5 is now tensioned, the recess 9 no longer engages with the cannula-side projection 11, so that, in another tensioning movement of the tensioning grip 7, the engaging member 8 when leaving the contact surface 14 is turned towards the stylet carriage 6 by the force of the spring 13. Therefore, the recess 10 of the engaging member 8 can now engage with the stylet-side projection 12, so that the stylet carriage 6 can be tensioned by the movement of the tensioning grip 7 and can be locked with the housing 4.

Now, the locking of the tensioned carriage with the upper shell 4*b* of the housing will be described. As can be seen in FIG. 5, the inner side of the upper half-shell 4*b* of the housing has, in the transverse direction next to the first key 19, two components projecting downwards, which are integrally formed in their base area. The component provided outside in the transverse direction forms a first cannula-carriage holding surface 18 for the first cannula snap-in hook 17 (see FIG. 2*a*). The component disposed inside in the transverse direction forms a second cannula carriage holding surface 26 for the second cannula snap-in hook 25 (see FIG. 2*a*). Both holding surfaces 18 and 26 are directed to the rear side and substantially extend in the vertical direction. Furthermore, both components have surfaces which are chamfered to the front side and along which the cannula snap-in hooks 17, 25 slide in the respective tensioning operation, thus being pressed downwards until their front sides get behind the holding surfaces 18, 26 and lock with the same.

Moreover, the component forming the second cannula carriage holding surface 26 has a recess 29 formed above the second cannula carriage holding surface 26, recessed towards the front side. The lug 28 of the release element 27 is immersed in said recess 29 when the cannula carriage 5 is in its non-tensioned initial position (see FIG. 11).

As can also be seen in FIG. 5, the inner side of the upper half-shell 4b of the housing has, in the transverse direction next to the first key 19, a component projecting downwards on the side opposite to the cannula carriage holding surfaces 18, 26, said component forming a stylet carriage holding surface 16 for the stylet snap-in hook 15 (see FIG. 2). The holding surface 16 is directed to the rear side and substantially extends in the vertical direction. Furthermore, the projecting component, which forms the stylet carriage holding surface 16, has a surface which is chamfered towards the front side and along which the stylet snap-in hook 15 slides during tensioning, thus being pressed downwards until its front side gets behind the holding surface 16 and locks with the same.

The tensioned biopsy gun 1 can be triggered in two ways. In a first mode, the first key 19 is firstly operated so that only the stylet 3 is triggered and, subsequently, the second key 20 is operated in order to trigger the cannula 2. In a second mode, the second key 20 is immediately operated, thereby first triggering the stylet 3 and, subsequently, when the stylet has completely moved forward, the cannula 2 is triggered.

Now, the first triggering mode shall be described.

Figure 3A:
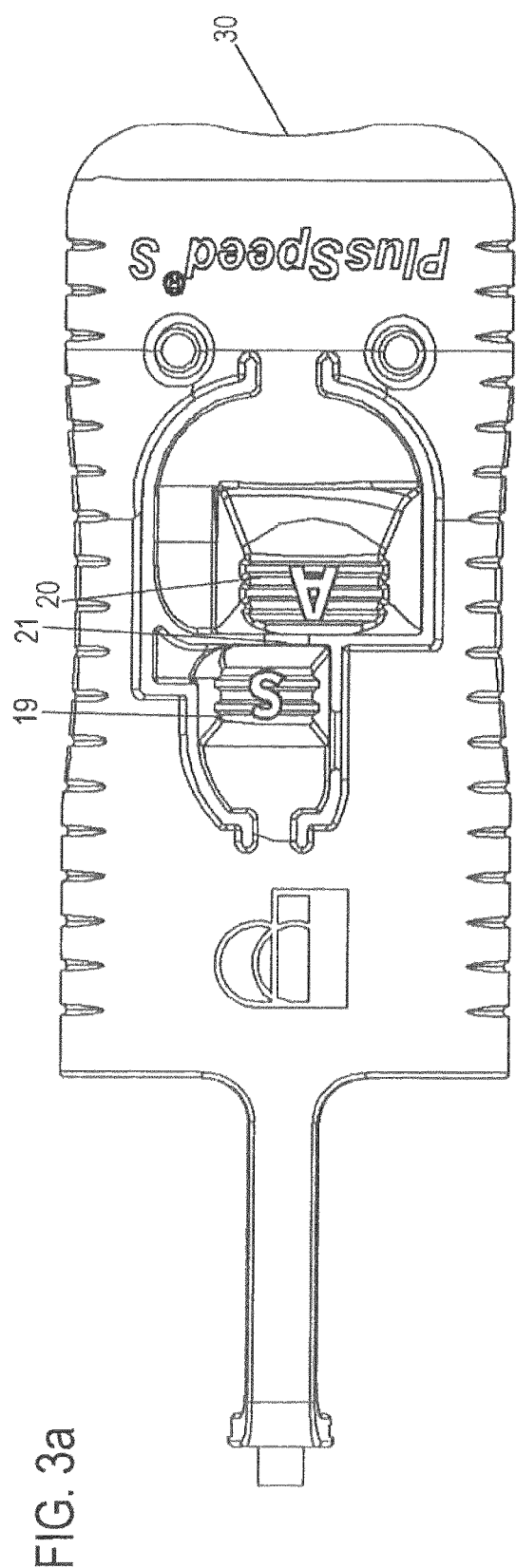
FIG. 3a is a top view of the upper half-shell of the housing.
Figure 3B:
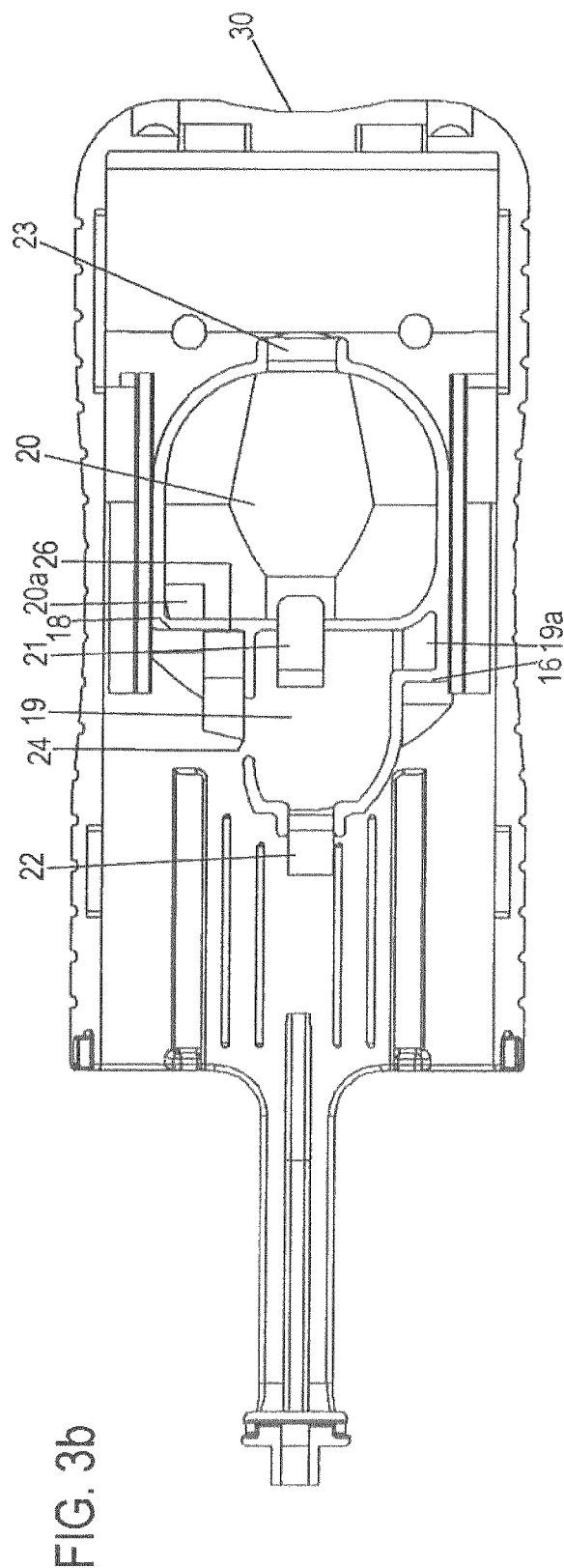
FIG. 3b is a bottom view of the upper half-shell of the housing.

As can be seen in FIGS. 3B and 5, the first key 19 is elastically fastened to the housing 4 by means of a main connecting element 22. The main connecting element 22 is disposed at the front side of the first key 19, integrally connects the first key 19 to the housing 4, and has a cross-sectional weakening ensuring the elasticity.

Furthermore, the first key 19 is integrally connected to the housing 4 by means of an additional connecting element 24. The additional connecting element 24 is disposed roughly within the area of the components providing the holding surfaces 18 and 26 and, thus, relative to the longitudinal direction, approximately in the middle of the first key 19.

On the side of the first key 19 that is opposite to the additional connecting element 24 in the transverse direction, a trigger projection 19a projects downwards. In the tensioned state of the stylet carriage 6, said trigger projection 19a acts on the stylet snap-in hook 15, so that, upon operation of the first key 19, the front side of the stylet snap-in hook 15 is released from the stylet carriage holding surface 16, and the stylet carriage 6 is moved forwards by the force of the coil spring.

In the state in which the stylet carriage 6 is already moved forwards but the cannula carriage 5 is still in its tensioning position, the trigger element 27 of the stylet carriage 6 has moved over the first cannula snap-in hook 25 of the cannula carriage 5 and has pressed the latter downwards, so that the engagement of the cannula snap-in hook 25 with the cannula carriage holding surface 26 has been released. In this way, the cannula carriage 5 can only be triggered when the stylet has been fully operated.

Besides, the additional connecting element 24 makes the first key 19, when operated, tilt about an inclined axis, which basically runs through the main connecting element 22 and the additional connecting element 24, so that the trigger projection 19a is safely pressed downwards.

As can be seen in FIGS. 3B and 5, the second key 20 is elastically fastened to the housing via a main connecting element 23. The main connecting element 23 is disposed at the rear side of the second key 20, it connects the second key 20 integrally to the housing 4, and it has a cross-sectional weakening ensuring the elasticity.

On the side opposite to the trigger projection 19a of the first key 19 in the transverse direction, a trigger projection 20a projects downwards from the second key 20. In the tensioned state of the cannula carriage 5, said release projection 20a acts on the cannula snap-in hook 17, so that, upon operation of the second key 20, the front side of the cannula snap-in hook 17 is released from the cannula carriage holding surface 18, and the cannula carriage 5 is moved forwards by the force of the coil spring.

Now, the second triggering mode shall be described.

When, in the state in which both carriages 5, 6 are tensioned, the second key 20 is operated, then the front side of the second key 20 acts on an operating lug 21 of the first key 19, extending under the second key 20 (see FIGS. 3B and 5). In this way, the first key 19 is operated along with the operation of the second key 20, so that, firstly, the stylet carriage 6 is triggered and moves forwards. During said movement, however, the cannula carriage is still held by the second cannula snap-in hook 25, which abuts on the cannula carriage holding surface 26 and cannot be operated by the second key 20. Simultaneously, however, the first cannula snap-in hook 17 is released from the first cannula carriage holding surface 18 by the operation of the second key 20, so that the cannula carriage 5 is only held by the second cannula snap-in hook 25.

When the stylet carriage 6 now moves further forwards, the trigger element 27 passes over the second cannula snap-in hook 25 and presses the latter downwards, so that it is released from the second cannula carriage holding surface 26 when the stylet carriage 6 has reached its relaxed initial position. Thus, the cannula carriage 5 is automatically triggered when the stylet carriage has advanced far enough.

In the same way as in the first mode, the lug 28 is immersed into the recess 29 here, too. The reason for this shall be stated below.

The biopsy gun 1 can be designed as a disposable device, the essential components being injection-molded parts constructed to be as light and material-saving as possible. At the same time, when the biopsy gun is used, e.g. for a prostate biopsy, large loads may be applied and may lead to a bending of the components. Moreover, the second cannula snap-in hook 25 has to be constructed such that it is, on the one hand, safely deformed by the chamfered surface on the component having the second cannula carriage holding surface 26, to then lock on the second cannula carriage holding surface 26; on the other hand, it has to be safely adapted to be operated, i.e. bent downwards, by the trigger member 27. Depending on the rigidity and load conditions, however, the case may arise that the cannula snap-in hook 25 is not pressed downwards by the trigger element 27, but that the cannula snap-in hook 25 presses the trigger element 27 upwards, thus preventing that the cannula snap-in hook 25 is released from the cannula carriage holding surface 26. This would lead to the cannula carriage not being triggered.

The immersion of the lug 28 on the trigger element 27 into the recess 29, which is part of the upper half-shell of the housing, ensures that the stylet carriage 6, particularly the section comprising the trigger element 27, is held in its position with respect to the vertical direction. In this way, it can be prevented that this section moves away upwards, so that the cannula snap-in hook 25 is always released safely.

As has already been stated, the housing 4 consists of two housing half-shells 4a and 4b having L-shaped frame elements 4a1 and 4b1, at the front ends of which a semi-cylindrical portion is formed, respectively, together forming a stub cone 4c serving as a cannula-guiding portion. At this point, the housing is exposed to particularly strong loads because the cannula 2 and the stylet 3 can be heavily bent e.g. during a prostate biopsy, thus applying lateral forces onto the stub cone 4c, said forces acting radially outwards on the inner side of the stub cone 4c. Therefore, unless further measures are taken, the danger arises that the half-shells of the housing get detached from each other here, so that a correct handling of the device is no longer guaranteed.

Therefore, the two frame elements 4a1 and 4b1 are locked with each other in the area of the stub cone 4c in both longitudinal directions opposing each other. For this, the L-shaped frame element 4a1 has, at the inside end of its short leg, projections 41 on both sides of a recess through which the cannula 2 is guided (see FIG. 2a). One half of the cone stub 4c is formed at the front side of the short leg (see FIG. 2b), two forked sections of the short leg with their level being lowered rearwards extending further towards the frame element 4b1. In each forked section, a recess 42 open towards the inner side between the forked sections is formed at the front side.

FIG. 5 shows the design of the short leg of the L-shaped frame element 4b1. Here, the second half of the cone stub 4c is formed at the end of the short leg. The surface of this end, facing rearwards, has a projection 43 fitting into the two recesses 42 of the frame element 4a1. The interaction of the projection 43 and the recesses 42 serves to hold together the ends of the short legs of the frame elements 4a1 and 4b1 in all directions perpendicularly to the longitudinal axis.

Moreover, the end of the short leg of the frame 4b1 has a projection 44 that extends on the rear side of the end towards the frame element 4a1 and can be brought into contact with the projection 41 of the frame element 4a1. Thus, the two frame elements 4a1 and 4b1 are locked at their ends in the first longitudinal direction of the biopsy gun 1.

Furthermore, the area of the end of the short leg of the frame element 4b1 is disposed in front of the forked sections of the end of the short leg of the frame element 4a1. Thus, the two frame elements 4a1 and 4b1 are locked at their ends in the second longitudinal direction, which is opposite to the first longitudinal direction.

Thus, the cone stub 4c, when mounted, can be exposed to large loads by the bent cannula, without the click-on connection being released unintentionally.

The housing half-shells 4a, 4b additionally comprise further locking elements, which reliably connect the housing half-shells 4a, 4b in the longitudinal direction and in the transverse direction.

The invention claimed is:

1. A biopsy gun having a cannula and a stylet guided in the cannula, the biopsy gun further comprising:
    a housing,
    a cannula carriage for moving the cannula,
    a stylet carriage for moving the stylet,
    a tensioning grip for tensioning the cannula carriage and the stylet carriage from an initial position into a tensioning position,
    an engaging member that is provided on the tensioning grip and has recesses adapted to engage with corresponding projections of the cannula carriage and the stylet carriage, wherein
    the engaging member is rotatably attached to the tensioning grip and is biased by a spring against a contact surface of the housing, wherein
    the tensioning grip comprises a section rotatably supporting the engaging member and comprising a spring receiving hole,
    the engaging member comprises a spring receiving groove, and
    a first end of the spring is inserted into the spring receiving groove, and a second end of the spring is inserted into the spring receiving hole, wherein
    the engaging member has a cannula-side recess and a stylet-side recess, the cannula carriage has a cannula-side projection, and the stylet carriage has a stylet-side projection, wherein
    the cannula-side projection is closer to the engaging member than the cannula-side projection is to the stylet-side projection, at least in the initial position of the engaging member, the contact surface, the cannula-side projection and the stylet-side projection are configured such that, in a non-operated position of the tensioning grip, the engaging member is held by the spring and the contact surface in such a rotational position, such that, upon operation of the tensioning grip, the cannula-side recess engages with the cannula-side projection so that, upon an operation of the tensioning grip, the engaging member is rotated by the engagement between the cannula-side recess and the cannula-side projection against the spring force towards the side of the cannula-side projection, so that the stylet-side recess cannot engage with the stylet-side projection when the cannula carriage is tensioned.

2. The biopsy gun according to claim 1, wherein
the contact surface of the housing is disposed on the side of the engaging member which corresponds to the stylet carriage.

* * * * *